United States Patent [19]

Segal

[11] Patent Number: 4,606,542

[45] Date of Patent: Aug. 19, 1986

[54] LIMB MUSCLE EXERCISING

[76] Inventor: David Segal, 229 Fuller St., W. Newton, Mass. 02165

[21] Appl. No.: 666,489

[22] Filed: Oct. 30, 1984

[51] Int. Cl.$^4$ ............................................. A63B 21/02
[52] U.S. Cl. ..................................... 272/137; 272/119
[58] Field of Search ..................... 128/25 R, 26, 80 B; 272/130, 119, 139, 126, 121, 120, 137, 142

[56] References Cited

U.S. PATENT DOCUMENTS 3,976,057  8/1976  Barclay ............................... 272/130

FOREIGN PATENT DOCUMENTS 295632  12/1916  Fed. Rep. of Germany .... 128/80 B

Primary Examiner—Richard J. Apley
Assistant Examiner—James Prizant
Attorney, Agent, or Firm—Charles Hieken

[57] ABSTRACT

A limb exerciser, such as for a leg, includes a brace hinged at the middle with upper padded members for snugly engaging the upper portion of a limb and lower padded members for snugly engaging the lower portion of a limb. Elastic hook-and-loop fasteners surround the members and the limb to firmly secure the members to the limb. A U-shaped portion extends above the center of the hinge and carries fulcrum assemblies on each leg of the U over which a resilient member rides. The ends of the resilient member are attached to upper studs at the far ends of the upper and lower assemblies. A second pair of resilient members may be connected between lower studs at the far end of each support assembly.

6 Claims, 4 Drawing Figures

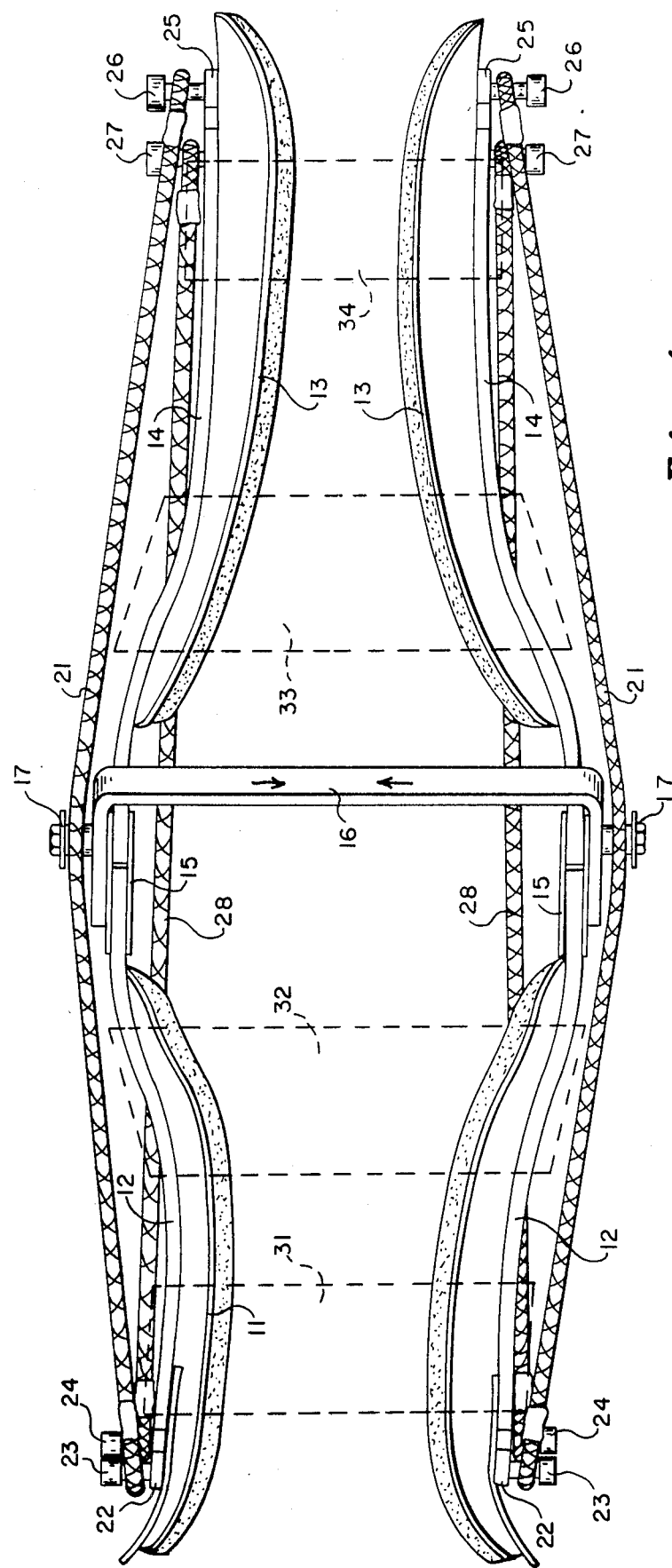

LIMB MUSCLE EXERCISING

The present invention relates in general to limb muscle exercising and more particularly concerns novel apparatus and techniques for exercising leg and arm muscles with apparatus that is relatively easy to install on a wide variety of leg and arm sizes while facilitating varying the nature of the exercise. The invention is relatively easy to use by unskilled personnel and allows the user to perform other activities while exercising.

After knee surgery it is common to treat patients with physical therapy to strengthen leg muscles inactive during recovery. It is also desirable to strengthen these muscles in a healthy person to enhance performance in athletic events, help prevent injury and for general well being. A number of exercising aids have been available for this purpose, such as weights attached to the ankle and weight or spring-loaded lines with a ring at the end for engaging the foot. Various ones of these prior art approaches have a number of disadvantages, such as inconvenient locations for using, limitations on muscles exercised and inconvenient to use.

It is an important object of this invention to provide improved apparatus and techniques for limb exercising.

According to the invention, there is a limb brace having upper means for engaging the leg portion above the knee, lower means for engaging the leg portion below the knee, and means for hingeably attaching the upper means to the lower means. There is fulcrum supporting means extending above the means for hingeably attaching for supporting upper spring means for resiliently interconnecting the upper means and the lower means so that when the upper means is fastened to the limb portion above the joint and the lower means fastened to the limb portion below the joint, moving the lower limb portion downward extends the spring means. There is also second spring means for interconnecting the upper means and the lower means below the means for hingeably connecting so that raising the lower limb portion extends the second spring means. Preferably, the first and second spring means may be detachably secured to the upper and lower means so as to enable performing a first set of exercises that strengthen muscles working against the first spring means and a second set of exercises that strengthen the limb muscles working against the second spring means.

Numerous other features, objects and advantages of the invention will become apparent from the following specification when read in connection with the accompanying drawing in which:

FIGS. 3 and 4 are side and top view of the embodiment of FIGS. 1 and 2 apart from the leg.

Figure 2:
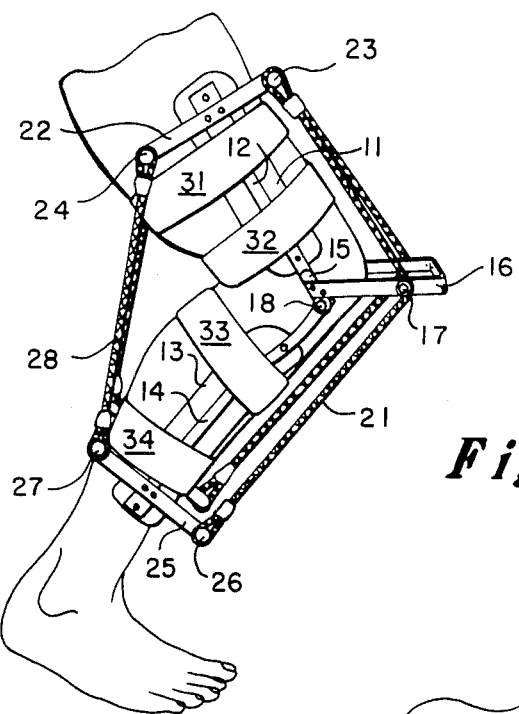
FIG. 2 is a perspective view of the embodiment of FIG. 1 with the leg contracted.
Figure 1:
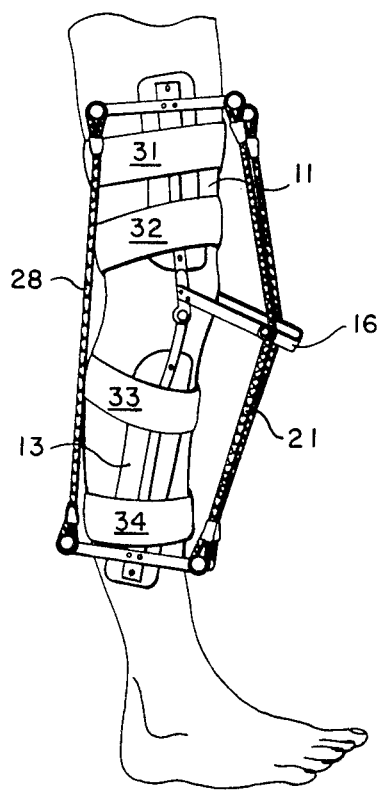
FIG. 1 is a perspective view of an embodiment of the invention with the limb extended.
Figure 3:
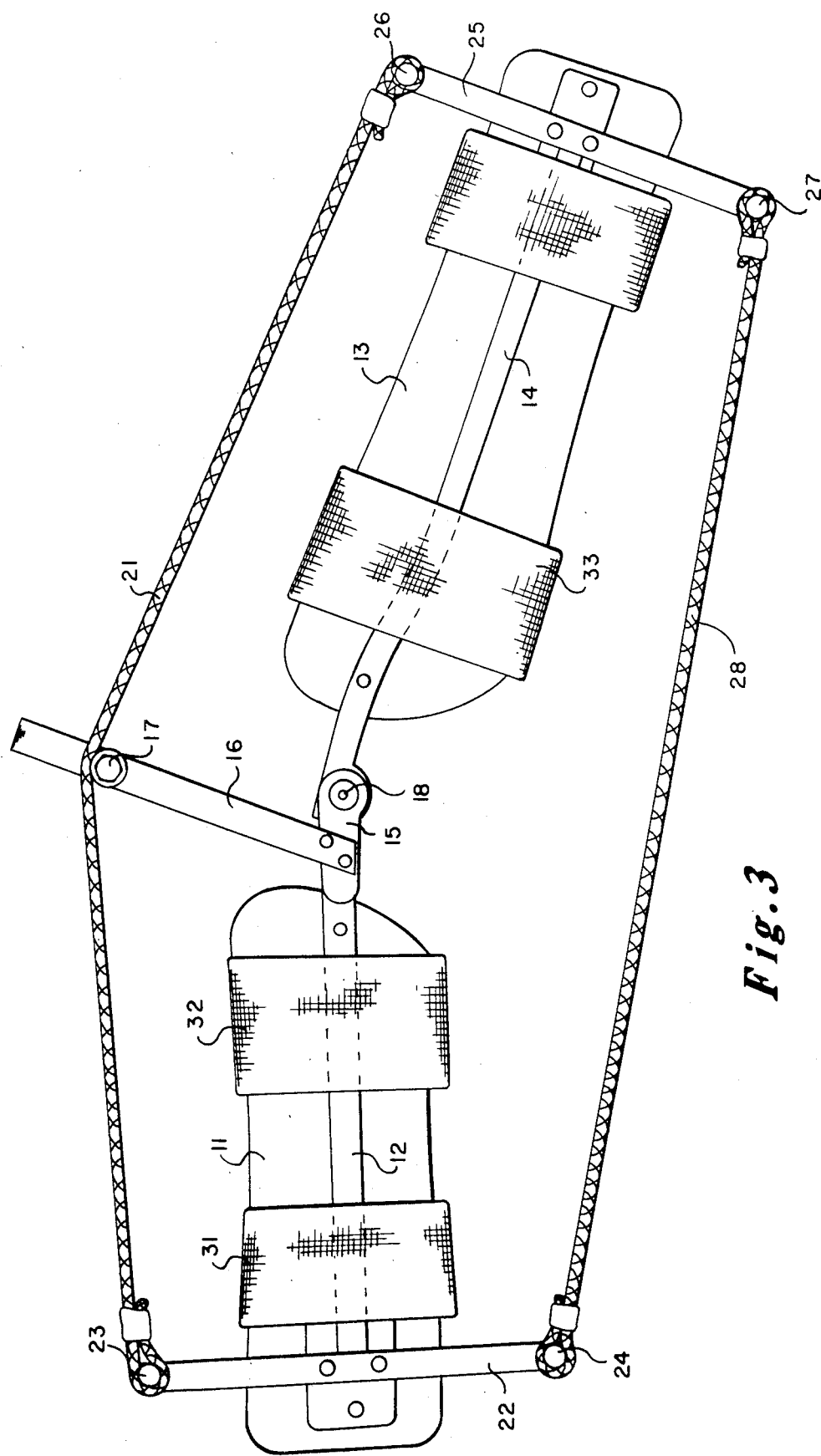

With reference now to the drawing, and all the FIGS. thereof, there is shown in FIGS. 1 and 2 perspective views of an embodiment of the invention attached to a leg with the leg extended and contracted, respectively, and in FIGS. 3 and 4 side and top views, respectively, of the embodiment of FIGS. 1 and 2 removed from the leg. The invention includes padded upper leg support portions 11 secured to upper rods 12. Similarly padded lower leg support members 13 are secured to lower rods 14. Lower rods 14 are hingeably connected at the top to hinge members 15 that are fastened to the lower end of upper rods 12 whereby the upper and lower portions are hingeably attached so that when fastened to the leg, the hinge axis corresponds substantially to the hinge axis of the knee.

A U-shaped member 16 extends upward from hinge member 15 forming an obtuse angle wth upper rod 12. The legs of member 16 carry bolt-washer-sleeve assemblies 17 located above the hinge axis 18 to define a fulcrum for upper elastic member 21. Member 16 may be adjusted to widen or tighten the brace for better fit around the limb.

Transverse rods 22 are secured to the upper end of rods 12 and carry at the ends upper studs 23 and lower studs 24. Similarly transverse rods 25 are fastened to the lower rods 14 and carry upper studs 26 and lower studs 27. Upper spring bands 21 have loops at each end surrounding studs 23 and 26 and extend over assemblies 17. Lower elastic members 28 are similarly looped at each end with the loops surrounding lower studs 24 and 27, respectively. Upper elastic hook-and-loop fasteners 31 and 32 and lower elastic hook-and-loop fasteners 33 and 34 are attached to the upper and lower portions and wrapped around the respective portions with upper and lower leg portions between upper member 11 and lower members 13, respectively, to clamp these leg portions between the respective members with the hinge axis 18 corresponding substantially to the joint axis. Fasteners 31 and 32 may be plain nonelastic straps.

Having described the structural arrangement of the invention, its mode of operation will be described. First, with elastic members 21 and 28 removed and hook-and-loop elastic fasteners 31, 32, 33 and 34 unwrapped, the invention is placed on a leg with the upper leg portion sandwiched between members 11 and the lower leg portions sandwiched between members 13 with hinge axis 18 coresponding substantially to the knee hinge axis. Telescopeing member 16 accommodates legs of different width. Fasteners 31, 32, 33 and 34 are then wrapped around members 11 and 13 and the leg portions therebetween to firmly secure the assembly to the leg. For a first exercise elastic membes 21 are fastened between upper studs 23 and 26 and over fulcrum assemblies 17 with the leg extended. The leg is then contracted and cycled between being extended and contracted to exercise appropriate muscles for a number of times. The exerciser may exercise while sitting and reading or watching television. The amount of exercise may be varied by varying the force exerted by the elastic members 21 in tension. For example, to provide more force, members 21 may be shorter when fully contracted, thicker or stronger.

After exercising with elastic members 21, these members may be removed, and elastic members 28 attached between lower studs 24 and 27 attached with the leg contracted. Extending the leg then exercises those muscles used in extension working against the restoring force of elastic members 28 in tension. These elastic members when connected as shown are resilient elastic means in tension. Resilient elastomeric means, such as these elastic members, embrace such a means that can be stretched beyond its original length to be in tensile stress, and upon immediate release of the stress, will return with force to its approximate original length.

In an exemplary embodiment of the invention the separation between upper studs 23 and 26 with the assembly in the position of the leg fully extended was substantially 19 inches while that between lower studs 24 and 27 was substantially 17 inches. A suitable length for upper elastic members 21 was substantially 18 inches made of elastic cord substantially ⅜" in diameter. Suitable length for elastic member 28 was substantially 11 inches of elastic cord substantially ¼" in diameter.

As examples of variations, hinges 18 may allow full joint motion or may be arranged for limiting part of the joint motion. Sometimes after surgery it is desirable to avoid full motion while exercising over part of the joint movement range. This limitation may be accomplished by placing a stud in one hinge. There are available braces with limited motion hinges.

As still another alternative, rods 12 and 14 may be telescoping to make the structure more compact and portable. This telescoping feature may also be useful in connection with acommodating limbs of different lengths.

Member 16 may take a number of different shapes, such as being circular, elliptical and other shapes and may accommodate limbs of different widths. It may be adusted by gliding, overlapping, screw or other adjusting techniques. It may be a telescoping member.

Fulcrum 17 may be attached to member 16 or independently to rod 12 or as an extension of hinge 15. The structural arrangement embodies the concept of effectively using limb muscles to extend a spring member, such as an elastic or spring over a fulcrum.

The invention may be used for strengthening the arm working around the elbow joint and the leg working around the knee joint. The invention allows a limb to which it is attached to be exercised separately without requiring manual assistance.

The invention may be embodied in still other different forms. For example, the elastic members could be coil springs or attached in a number of different locations and in a number of different forms, for example, spiral springs around hinge axis 18. For example, elastic members could be connected between upper studs 23 and lower studes 27 or between lower studs 24 and upper studs 26, crossing over or under the joint from inside out or vice versa. Numerous techniques may be used for fastening the upper and lower portions to upper and lower leg portions, respectively. It is evident that those skilled in the art may now make numerous other uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Limb exerising apparatus comprising,
    upper means for snugly engaging the upper portion of a limb,
    lower means for snugly engaging the lower portion of a limb seprated from the limb upper portion by a joint pivotable about a joint axis,
    means for hingeably attaching said upper means to said lower means about a hinge axis substantially coinciding with said joint axis,
    and resilient elastomeric means in tension connected between said upper means and said lower means for exerting a torque about the axis of said means for hingeably attaching against which limb muscles may work when the upper portion of a limb is secured to said upper means and the lower portion of said limb is secured to said lower means and said limb is extended and contracted about said joint and for allowing movement against said tension between said upper and lower portions while exercising said limb.

2. Limb exercising apparatus in accordance with claim 1 and further comprising,
    fulcrum means above said hinge axis for receiving an elastic member comprising said resilient means,
    said elastic member being connected between said upper means and said lower means and extended over said fulcrum means.

3. Limb exercising apparatus in accordance with claim 2 wherein said upper means and said lower means have studs means to which the ends of said resilient member are attached.

4. Limb exercising apparatus in accordance with claim 3 wherein said stud means comprise upper and lower stud means,
    said lower stud means being for receiving a resilient member comprising said resilient means so that extending said limb stretches the latter resilient member.

5. Limb exercising apparatus in accordance with claim 1 wherein said upper and lower limb portions form an acute angle with vertex on said joint axis when said limb is contracted embracing the inside of said joint and further comprising,
    fulcrum means outside said acute angle for receiving an elastic member comprising said resilient means for providing a tensile force tending to move said limb to the extended position while allowing said limb to move toward the contracted position while exercising said limb by moving said limb portions about said joint axis in a sector embraced by said acute angle.

6. Limb exercising apparatus in accordance with claim 5 wherein said fulcrum means comprises a member of adjustable width for accommodating limbs within a substantial range of widths.

* * * * *